United States Patent [19]

Smith

[11] Patent Number: 4,979,955
[45] Date of Patent: Dec. 25, 1990

[54] POWER ASSISTED PROSTHETIC HEART VALVE

[76] Inventor: Robert M. Smith, 2B Talcott Forest Rd., Farmington, Conn. 06032

[21] Appl. No.: 184,300

[22] Filed: Jun. 6, 1988

[51] Int. Cl.$^5$ .............................................. A61F 2/24
[52] U.S. Cl. ........................................ 623/2; 137/514
[58] Field of Search ............................. 623/2; 137/514

[56] References Cited

U.S. PATENT DOCUMENTS

| | | | |
|---|---|---|---|
| 3,233,610 | 5/1963 | Wade | 604/9 |
| 3,370,305 | 2/1968 | Goott et al. | 623/2 |
| 3,476,355 | 11/1969 | Sherwood | 251/65 |
| 3,491,756 | 1/1970 | Bentov | 604/52 |
| 3,696,674 | 10/1972 | Spencer | 623/2 |
| 3,926,175 | 12/1975 | Allen et al. | 600/30 |
| 3,927,422 | 12/1975 | Sawyer | 623/1 |
| 3,959,827 | 6/1976 | Kaster | 623/2 |
| 3,974,854 | 8/1976 | Kurpanek | 623/2 |
| 4,038,702 | 8/1977 | Sawyer | 623/2 |
| 4,601,309 | 7/1986 | Chang | 137/514 |
| 4,605,408 | 8/1986 | Carpentier | 623/2 |
| 4,661,107 | 4/1987 | Fink | 128/419 PS |
| 4,769,032 | 9/1988 | Steinberg | 623/2 |

FOREIGN PATENT DOCUMENTS

| | | | |
|---|---|---|---|
| 3128704 | 2/1983 | Fed. Rep. of Germany | 623/2 |
| 0608368 | 1/1979 | Switzerland | 623/2 |

*Primary Examiner*—Randall L. Green
*Assistant Examiner*—Stephanie L. Iantorno
*Attorney, Agent, or Firm*—Fishman, Dionne & Cantor

[57] ABSTRACT

A power assisted mechanism is applied to prosthetic valves as a way of initiating closure of the valve at the appropriate moment in the pump cycle to minimize regurgitation, to create an electromagnetic force to decelerate completion of valve closure to minimize traumatic hemolysis of red blood cells, and to provide a negative charge to the valve as a way of repelling red blood cells and platelets to reduce thrombogenic phenomena and to provide a cushioning force field effect to reduce red blood cell hemolysis associated with turbulent flow across the valve. In one embodiment, a known tilting disc valve comprising an annular frame or cage and a disc pivotably mounted thereon has a fixed electromagnet attached to the annular frame and a permanent magnet attached to the tilting disc. When energized, the resultant magnetic field will repel the permanent magnet located on the free floating disc thereby closing the valve. An important feature of the present invention involves determining the appropriate moment in the cardiac cycle to initiate active closure of the valve. In a preferred method of triggering or initiating closure of the valve, the electrical activity of the heart is monitored and at the appropriate time in the cardiac cycle, as determined by the electrical wave form, active closure of the device may be initiated. This can be accomplished by using a monitoring and control circuit which is similar to known monitoring and control circuits associated with pacemaker and implantable cardioverter/defibrillator devices.

15 Claims, 5 Drawing Sheets

POWER ASSISTED PROSTHETIC HEART VALVE

BACKGROUND OF THE INVENTION

This invention relates generally to a valve for controlling the unidirectional flow of a pulsatory fluid. More particularly, this invention relates to a new and improved valve prosthesis which provides for the nontraumatic control of body fluid flow through the use of active means which consists of power generated by electromagnetic energy. This invention is particularly well suited for use as a valve prosthesis for controlling blood flow through the heart of a human or animal.

Artificial valves, both those used as prosthetic devices within the human and animal body and those used to control the flow of body fluids externally, have long been known to the medical profession. The prior art valves used primarily as prosthetic devices have taken many forms in an attempt to replicate the function of the natural valves which they replace. None of these prior art valves, however, has fully achieved the replication of a naturally occurring valve. Lack of success has resulted in part from problems with long term durability of the valve itself and from differences between actual and measured fluid flow area provided by the valve which has resulted in undesirable pressure gradients across the valve. In addition, prior art valves increase rather than reduce or eliminate, the turbulence created by the passage of fluid through and the subsequent closure of the valve. Such turbulence results in greatly increased hemolysis when the fluid flowing through the valve is blood.

Prior art prosthetic valves conform, for the most part, to three general types including ball and cage valves, tissue valves and disc type valves. The ball and cage valve, such as that described in U.S. Pat. No. 3,416,159, is usually constructed of silicone rubber, is susceptible to variance in shape, fractures of the ball surface and subsequent lipid infiltration into the ball. Additional complications which often accompany this type of valve include fibrin clot formation, which further interfers with the movement of the ball in the cage, and thrombosis. Because of these complications, the patient with this type of prosthesis must undergo continuous anticoagulant therapy. Moreover, since the ball portion of the valve must be located in the center of the cage to allow proper functioning of the valve, fluid flow through this type of valve cannot be central, as in a natural valve, but is directed through the valve around the periphery of the ball. The turbulence resulting from this, coupled with the turbulence created by closure of the valve, causes a higher level of hemolysis and blood cell damage that is undesirable. The presence of the ball in the center of the blood vessel also imparts an unnatural radial component to the flow of blood within the vessel producing injury to the walls of the vessel against which the radial component is directed. Ball and cage valves are large in size and therefore can present difficulties in insertion. They have also been disturbing to some persons into whom they have been inserted because of the audible sound detectable upon closing. Attempts to correct the deficiencies of the ball and cage type valve by replacing the ball with a disc shaped element have generally been unsuccessful.

A second type of prior art valve, generally referred to as a tissue valve, is composed of a stent or mounting ring to which human or animal tissue has been attached in a form which approximates the flaps in a natural valve. However, the long-term durability of these valves is still of concern. Construction of the tissue valve from cadaver material such as fascia lata results in a valve with low durability because of rapid tissue degradation and stiffening and has led to tissue dysfunction and subsequent valve immobility. Moreover, since these valves rely entirely on back pressure for closure, closure is accompanied by increased trauma to the blood cells and the greater likelihood of valve incompetence than encountered with a natural valve.

A third category of prosthetic valve is the disc type, which is generally formed of an annular base to which a disc-shaped valving member is secured, either by means of a magnetic hinge, as in U.S. Pat. No. 3,370,305 to Goot, by means of an eccentrically-placed stem, as in the Modified University of Capetown Prosthesis described by Ellis et al, in The Annals of Thoracic Surgery 23:26-31, 1977, or by means of a rod along which the disc can be displaced, as in U.S. Pat. No. 3,959,827 to Kaster. Although fluid flow through this type of valve is more centralized than through the ball and cage valve, increased hemolysis results from turbulence created by fluid flow through the valve. In addition, injury to the walls of the blood vessel beyond the valve results from the radial components imparted to the blood flow caused by the presence of the valve disc in the blood stream. Moreover, use of this valve necessitates the institution of long-term anticoagulant therapy because of the high level of thrombogenesis which accompanies the use of the valve. As reported in The Annals of Thoracic Surgery 23:26-31, 1977, Ellis et al discontinued use of one type of tilting disc prosthesis, in part because of the excessive incidence of thromboembolism and in part because the effective valve orifice area, after the valve had been in place, was usually considerably less than the measured orifice area before insertion.

The tilting disc is designed to pivot on an off center axis. To move from its closed position to its open position, the disc rotates on its axis to some position less than 90 degrees from its closed position. The valve structure has a mechanical stop to inhibit the disc from rotating to a position completely parallel to the direction of flow. Therefore when reverse flow occurs, the disc will be inclined to rotate back to its closed position because the force created by the reverse flowing fluid will be greater on one side of the disc than on the other. While repositioning the disc from its open position to its closed position, a finite amount of fluid (termed "regurgitationis allowed to pass through the valve in the reverse direction because the valve is not able to close instantaneously. Paradoxically, the quantity of reverse flow is minimized by reducing the pivot rotational angle of the disc and the quantity of laminar-forward flow is maximized by increasing the pivot rotation angle of the disc parallel to the direction of flow. In other words, one can increase laminar flow in the forward direction at the cost of regurgitation of the reverse direction.

In U.S. Pat. No. 3,959,827, Kaster discloses one embodiment of a disc type valve in which the closing of the valve is assisted by means of a permanent magnet located in the disc valving member. Although this permits a smoother closing than is possible without the magnet, the disc valve disclosed in U.S. Pat. No. 3,959,827 still suffers from the other drawbacks generally common to disc type valves. Forman et al reported in The Journal of Thoracic and Cardiovascular Surgery 75:595-598, 1978, that they no longer recommended the use of a tilting disc valve similar to the one disclosed in U.S. Pat. No. 3,959,827, in large part because of a high incidence of embolism and valvular thrombosis, but also because the effective orifice area of the valve was less than the actual orifice area. In addition, they found this type of valve demonstrated no clear hemodynamic advantage over other available prosthesis.

Valves used for medical purposes in which valve closing is magnetically assisted are also disclosed in U.S. Pat. Nos. 3,233,610 to Wade, 3,495,620 to Raimondi et al and 3,926,175 to Allen et al. The valves described in U.S. Pat. Nos. 3,233,610 and 3,495,620 provide fluid flow orifices through only a portion of the valve diameter, thus resulting in a slow fluid flow area in relation to valve diameter. The magnetically actuated valve disclosed in U.S. Pat. No. 3,926,175 is incapable of operating in response to fluid pressure within a body vessel and is thus unable to operate automatically to cause unidirectional flow of a pulsatory fluid. Magnetic repulsive forces have been used to aid valve operation as illustrated in U.S. Pat. No. 3,476,355 to Sherwood but has never been used to prevent traumatic valve operation which could result in injury to body fluids.

Other more recent magnetically assisted artificial heart valves are disclosed in U.S. Pat. No. 4,417,360 to Moasser and U S. Pat. No. 4,605,408 to Carpentier. Moasser discloses a prosthetic valve comprised of an annular mounting structure to which is attached at their proximal ends two opposed, spaced flexible flaps. These flaps include at their distal ends permanent magnetic members with sufficient magnetic force to prevent traumatic closure and to reduce the systolic pressure required upon opening. Carpentier relates to a prosthetic heart valve of the disc type which uses two small permanent magnets to enhance opening of the valve with the two magnets exerting a controlled repellant effect on one another. Carpentier also states that the permanent magnetics may be electromagnetic, but there is no disclosure of how this would be accomplished.

SUMMARY OF THE INVENTION

The above-discussed and other drawbacks and deficiencies of the prior art are overcome or alleviated by the power actuated valve prosthesis of the present invention. In accordance with the present invention, power assisted means are provided for:

(1) initiating closure of a valve at the appropriate moment in the cardiac cycle to minimize regurgitation;

(2) creating an electro-magnetic force to decelerate completion of valve closure to minimize traumatic hemolysis of red blood cells.

In addition, the present invention provides a negative electrical change to the valve as a means of repelling red blood cells and platelets to reduce thrombogenic phenomena and to provide a cushioning force field effect to reduce red blood cell hemolysis associated with turbulent flow.

In one embodiment of the present invention, a known tilting disc valve comprising an annular frame or cage and a disc pivotably mounted thereon has a fixed electromagnet attached to the annular frame and a permanent magnet attached to the tilting disc. When energized in one polarity, the resultant magnetic field will repel the permanent magnet located on the free floating disc thereby closing the valve. When energized in the opposite polarity the electro-magnet will decelerate closure and/or attract the free floating disc to its open position. In another embodiment, the electromagnet is mounted in a position on the valve frame so that when energized, the magnetic field produced will draw the valve flap into a closed position. In both embodiments, power assisted means is used to actively alter the relative position of the valve flap within the frame in which it is contained. The electromagnets are designed and located strategically in such a way as to minimize obstruction and generation of turbulence. In addition, each valve, with its modification, maintains the ability to function as a passive valve (leaflet will continue to respond to changes in pressure gradients).

An important feature of the present invention involves determining the appropriate moment in the cardiac cycle to initiate active closure of the valve. More than one method is available to accomplish this task. In one embodiment, pressure sensors could be used to determine the proper moment to initiate active closure of the valve. A single or multiple sensor could be mounted in either side of the valve frame and when a defined minimum or maximum level was detected, the initiation of active closure would be evoked. In a second and preferred method of triggering or initiating closure of the valve, the electrical activity of the heart is monitored and at the appropriate time in the cardiac cycle, as determined by the electrical wave form, active closure of the device may be initiated. This can be accomplished by using a monitoring and control circuit which is similar to known monitoring and control circuits associated with pacemaker devices.

The use of a valve in accordance with the present invention which can actively initiate closure at the appropriate movement in the cardiac cycle will provide many important benefits and improvements in reduction of regurgitation and an overall increase in efficiency of the heart.

The present invention also utilizes a negative charge to the valve as a way of repelling red blood cells and platelets in order to reduce thrombogenic phenomena and to provide a cushioning force filed effect to reduce red blood cell hemolysis associated with turbulent flow across the valve.

The above-discussed and other features and advantages of the present invention will be appreciated and understood by those of ordinary skill in the art from the following detailed description and drawings.

BRIEF DESCRIPTION OF THE DRAWINGS:

Referring now to the drawings, wherein like elements are numbered alike in the several FIGURES.

DESCRIPTION OF THE PREFERRED EMBODIMENT

This invention relates to a power assisted heart valve which utilizes electromagnetic means to initiate closure of the valve at the appropriate and most efficient point in the cardiac cycle. The present invention will be described in conjunction with several well known tilting disc valves (FIGS. 1 and 2) and a well known bileaflet valve (FIG. 3). However, it will be appreciated that the embodiments of FIGS. 1, 2 and 3 are by way of example only; and that the present invention may be used with many other types of heart valves such as the Omni Science valve as will be clear from the following discussion.

Figure 1:
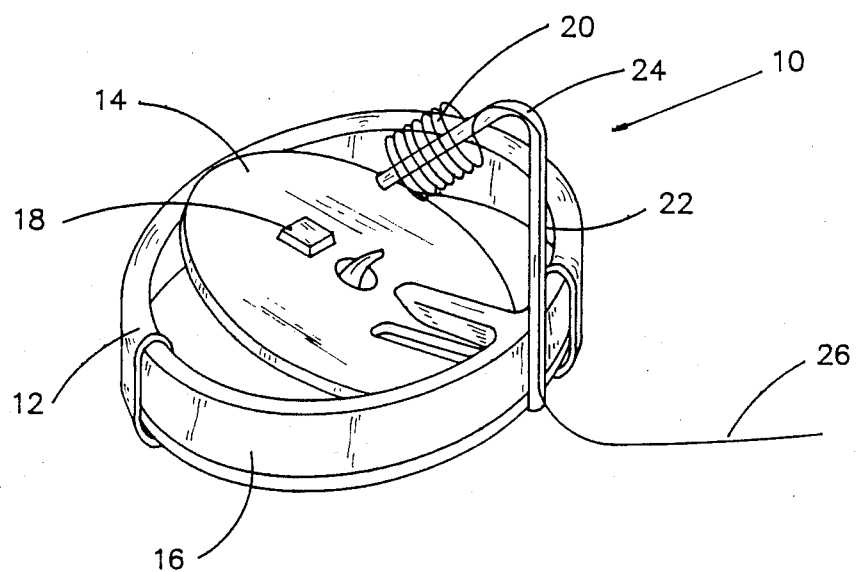
FIG. 1 is a perspective view of a first embodiment of the present invention using a tilting disc valve.

Referring now to FIG. 1, a first embodiment of a power assisted heart valve in accordance with the present invention is shown generally at 10. Valve 10 is similar to a well known tilting disc valve commercially available from Metronic, Inc. and known as a Hall Medtronic Valve. Valve 10 includes an annular frame or cage 12 having a disc 14 pivotably mounted thereon in a known manner to permit the disc 14 to be free floating. In the FIGURE, the disc is shown partially open. A ring of fabric 16 surrounds the exterior of frame 12 also in a known manner.

In accordance with the present invention, a small permanent magnet 18 is bonded or otherwise attached to the upper surface of disc 14 so that permanent magnet 18 travels in synchronization with disc 14. An electromagnet 20 is fixedly mounted to annular frame 12 by an arm 22. Arm 22 has a bent section 24 which acts to align electromagnet 20 with the path swept out by permanent magnet 18 when disc 14 is tilted (pivoted). Electromagnet 20 may be constructed in any known manner such as a simple coil of metal wire wrapped about arm 22. A lead 26 is connected to electromagnet 20 to selectively power the electromagnet 20 as will be discussed hereinafter. Lead 26 is electrically isolated from arm 22. It will be appreciated that by properly orienting permanent magnet 18, electromagnet 20, upon powering, will either repel or attract magnet 18 and hence disc 14.

Figure 2:
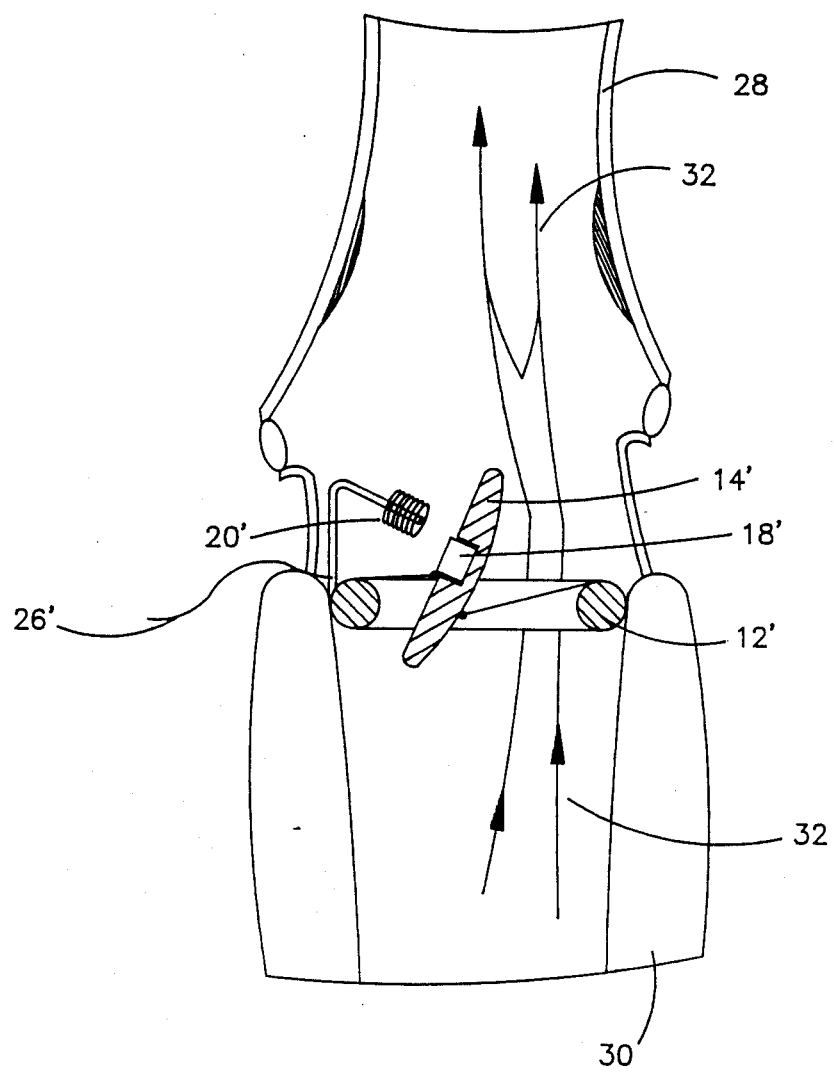
FIG. 2 is a cross-sectional elevation view of the tilting disc valve of FIG. 1 shown in an artery.
Figure 3:
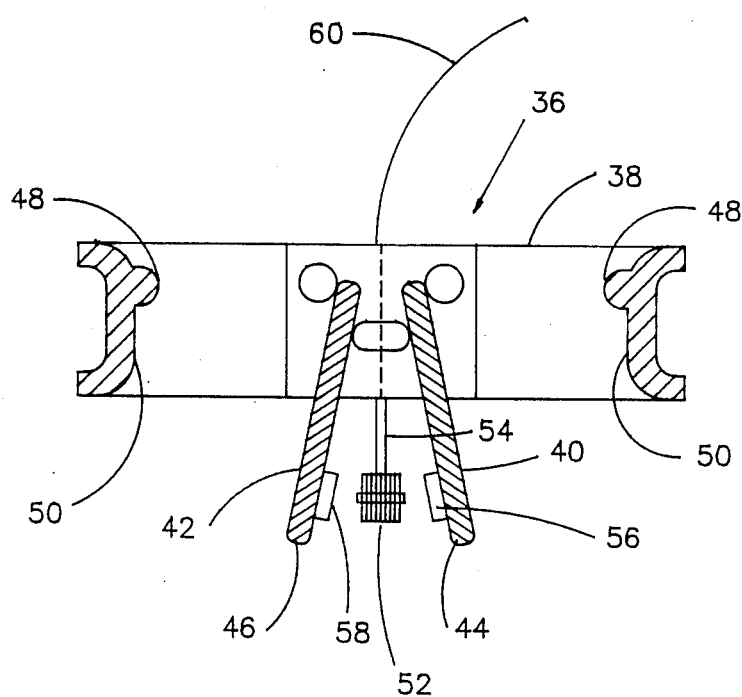
FIG. 3 is a cross-sectional elevation view of a second embodiment of the present invention using a bileaflet valve.
Figure 5:
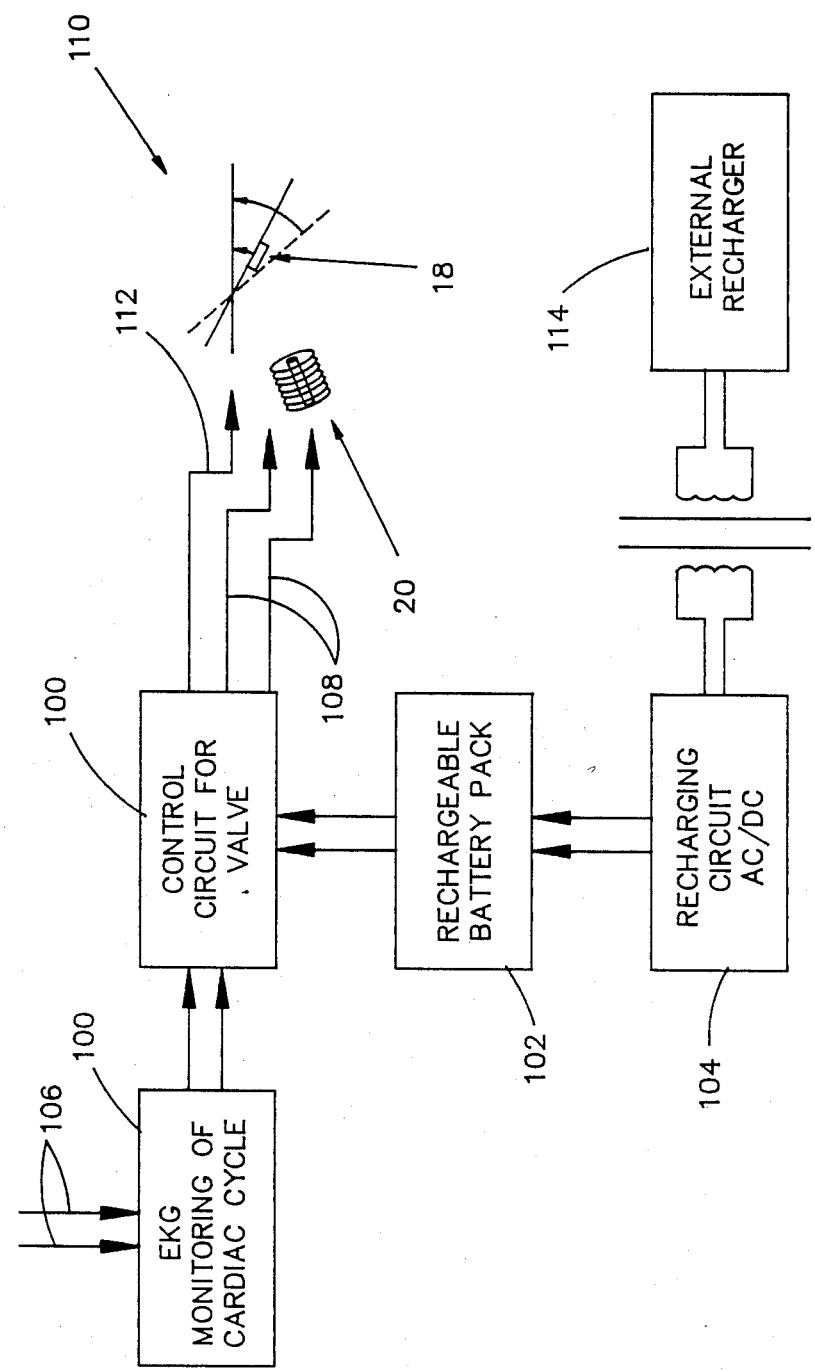
FIG. 5 is a schematic diagram of the power assisted prosthetic heart valve in accordance with the present invention.

In FIG. 2, a tilting valve commercially available from Bork-Shiley is shown generally at 27 after being surgically installed in the aorta 28 at the juncture of the left ventricle 30. The valve frame 12' is oriented such that arm 22' and electromagnet 20' extend into aorta 28. Lead 26' is threaded through the wall of the aorta to a controller device (FIG. 5). The flow of blood through the left ventricle 30 and aorta 28 is indicated by the arrows 32. Thus, valve 27 is shown with disc 14' in the fully open position wherein permanent magnet 18' and electromagnet 20' are relatively close in proximity. As will be discussed below, at an appropriate point in the cardiac cycle, electromagnet 20' is energized producing an electromagnetic field which will repel the electromagnetic field produced by permanent magnet 18'. As a result, disc 14' will move, closing the angle relative to its frame prior to influential changes in pressure gradients across the valve.

FIG. 3 illustrates the use of a power actuated (e.g. electromagnetic) heart valve in conjunction with a well known bileaflet valve shown generally at 36. Like valve 10 of FIG. 1, valve 36 comprises an annular frame 38 having a pair of oppositely disposed semi-circular flapper plates 40 and 42 pivotally mounted in frame 38 to permit free movement between the open position shown in the FIGURES to a closed position wherein the edges 44, 46 of plates 40, 42 contact the annular ridge 48 along the interior surface 50 of frame 38.

In accordance with the present invention, and in a manner similar to that illustrated in FIG. 1, an electromagnet 52 is fixedly attached by a rigid arm 54 to frame 38. Similarly, each flapper plate 44 and 46 is provided with a small permanent magnet 56 and 58 so that when electromagnet 52 is powered (via electrical lead 60), the magnetic field produced by electromagnet 52 will repel both permanent magnets 56 and 58 to thereby urge flapper plates 40, 42 against annular ridge 48 and effectively accelerate closure of the valve.

In all of the embodiments of FIGS. 1-3, the polarity of the electro-magentic may be reversed just prior to valve closure. This sudden reversal in polarity will act to dampen or reduce traumatic hemolysis of red blood cells.

In addition, the open angle of the leaflets for each valve type could be increased to allow for greater near laminar flow in the forward direction. Increasing the near laminar flow would reduce turbulence and underirable pressure gradients with forward flow. The increased angle would inherently create more regurgitation during closure of the valve in the passive mode. However, the increased regurgitation could be eliminated by involving the avtive closure mechanism.

A key feature of the present invention is that the powering of the electromagnet is carefully controlled in synchronization with the cardiac cycle. It is this controlling feature which permits the power actuated heart valve of the present invention to overcome and improve upon many of the problems and deficiencies of prior art heart valves.

In a less preferred embodiment, pressure sensors are used to determine the proper moment to initiate active closure of the valve. In this embodiment, single or multiple sensors may be mounted on either side of the valve frame and when a defined minimum or maximum level is detected, the initiation of active closure will be evoked.

Figure 4:
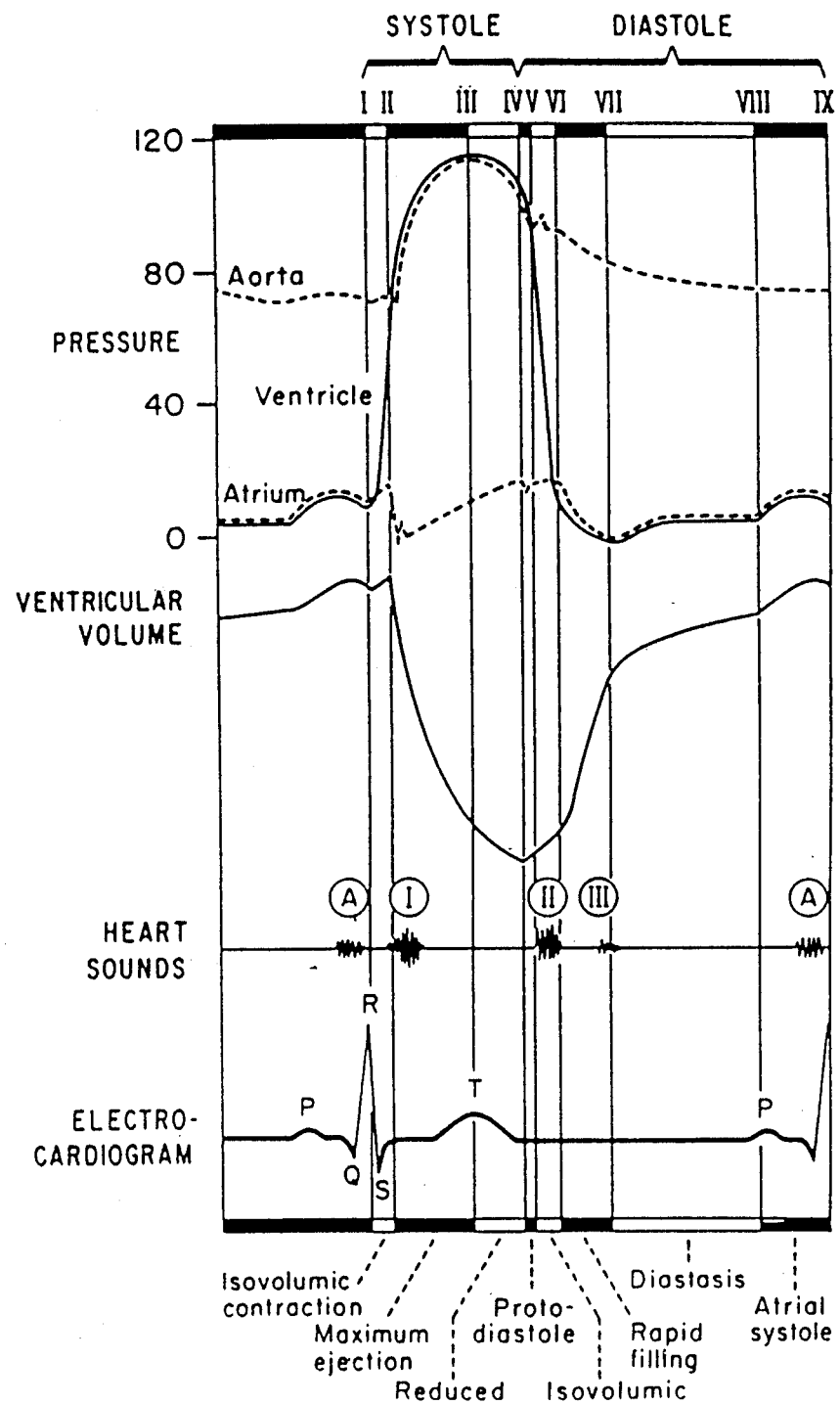
FIG. 4 is a graphical representation of a cardiac cycle on a Wigger diagram.

In a more preferred embodiment, active closure of the heart valve is effected by monitoring the electrical activity of the heart (EKG) and at the appropriate moment in the cardiac cycle (as determined by the electrical wave form), powering the electromagnet to actively close the valve. It is important that the details of the cardiac cycle and its representation on the Wigger diagram (FIG. 4) be understood in order to appreciate how this method is employed to initiate active closure of the electromagnetic valve of the present invention. On the diagram provided in FIG. 4, the horizontal or X axis represents time. One complete cycle is represented which would make a duration of 1 second at a heart rate of 60 beats per minute. On the vertical or Y axis, multiple factors are represented including electro-cardiogram (electrical activity of the heart), heart sound, ventricular volume and pressure. These four parameters are superimposed onto the same time axis so that an appreciation of the coordinated activities may be visualized.

On the Y-axis labeled Heart Sounds, the regions labeled as I and II are of particular interest to the present invention. Region I (the first heart sound) represents closure of the AV valves (Atrial-Ventricular valves i.e. the mitral and tricuspid valves) and region II corresponds to the closure of the aortic and pulmonary valves. These two regions correspond to specific regions on the electro-cardiogram depicted on the Y-axis below the heart sound axis. Approximately the peak of the QRS spike represents the initial closure of the AV valves. Shortly after the T-wave, perhaps during Protodiastole phase in the X-axis, initial closure of the aortic valve begins. Using a well known state-of-the-art pacemaker type device and signal processing techniques routinely employed by electrical engineers, a circuit may be used to initiate active closure of an AV or aortic valve at the appropriate time in the cardiac cycle. A similar approach has been proven, for example, with the Intra-aortic balloon assisted pumps used in common practice in modern hospital settings. (See, e.g., Clinical Application of Intra-Aortic Balloon Pump. Hooshang Bolooki, M.D., 2nd Edition 1984). Common threshold spike detection circuitry is utilized to sense the R-spike of the QRS complex and the R—R interval is measured to calculate heart beat rate. QRS detector circuits are commonly used in on-demand pacing and cardioverting as described in U.S. Pat. No. 4,548,209 assigned to Medtronic.

In U.S. Pat. No. 4,621,617 to Sharma, there is disclosed an artificial heart strengthening device which uses electromagnetic force to induce pulsating motion to pump the heart. The selective pulsing is triggered by a pacemaker type control system which is electrically synchronized with the natural activity of the heart. U.S. Pat. No. 4,302,854 to Runge relates to a compressible shunt which aids in pumping blood to or from the heart. The shunt includes a compressible body having two opposed plates, one of which is ferromagnetic. When an electromagnet exterior of the body is activated, the plates are attracted to one another forcing the shunt to compress and thereby pump blood. As in Sharma, a synchronizing method is used to activate the shunt in conjunction with the beat of the heart. In a paper entitled The Use of QT Interval to Determine Pacing Rate; Early Clinical Experience, Richards et al, the authors describe a modified Vitatron microprocessor based pacer which was adapted to detect the T-wave from an EKG signal and to calculate the QT interval. The QT interval is used to determine an appropriate pacing rate for the pacemaker.

The numerous examples set forth above illustrate that detecting R and T wave shapes in the EKG which correspond to closure of A-V and Aortic-pulmonic valves is conventional and well known.

By taking advantage of the consistency of the EKG of the heart, one can predict when the heart valve will need to be closed and can actively initiate closure as a means of reducing regurgitation. For example, just as the left ventricle is approaching a full supply of blood, (i.e. pre-isovolumic contraction), a prosthetic power assisted MITRAL valve in accordance with the present invention could be initiated to close just prior to contraction of the left ventricle. Providing this active closure will reduce regurgitation in the reverse direction and would increase the stroke volume in the forward direction thereby increasing the cardiac output. In a similar fashion, the aortic valve may be initiated to close at the tail end of the systolic or ejection phase thereby reducing backflow of blood into the left ventricle. Achieving concise closure will also maintain greater blood pressure in the aorta distal to the valve during diastole which will increase the degree of coronary artery profusion of the myocardium. In effect, active closure will increase the efficiency of the heart.

The paper *Regurgitation of Prosthetic Heart Valves: Dependence on Heart Rate and Cardiac Output* (Dellsperger et al, 1983) addresses the issue of regurgitation by using a pulse duplicator system to evaluate a wide spectrum of commercially available prosthetic heart valves. It should be apparent that all valves have some quantity of regurgitation, it is only a matter of how much. In this paper the researchers have measured the quantity of regurgitation as a function of both the cardiac output and the heart rate. They were able to illustrate that the quantity of regurgitation will increase with an increase in heart rate and a decrease in cardiac output. In one example, it was shown that with a heart rate of 140 beats/min and a cardiac output of 2 liters/min, the Bjork-Shiley Convexo Concave valve has a regurgitation of 36.5%. Note, decreased cardiac output and tachycardia (increased heart rate) are common occurrences in patients with congestive heart failure (CHF). Clinically significant incompetence occurs at regurgitant flows as low as 20 to 30% of the forward stroke volume. In this study, backflow in the "normal" range of operation was approximately 10%, which is not considered clinically significant. However, the hinged leaflet valves have total regurgitant fractions of 20% once cardiac output is 4 liters/min and heart rate is 110 beats/min. As a patient goes into congestive heart failure, the natural response is for the heart to increase the heart rate in an attempt to maintain an adequate arterial blood pressure. The increased heart rate promotes increased regurgitation, thus the patient may enter into a futile cycle which may lead to death. It is also believed that the chronic use of prosthetic valves have a gradual detrimental effect on the myocardium (i.e. hypertrophy) which could be further minimized by the improved power actuated valve of the present invention.

An electromagnetically powered assisted heart valve will increase the efficiency of the heart and relieve it of some unproductive strain. In a paper entitled *Late Results of Valve Replacement Surgery* the authors state that between 80% and 90% of all late deaths will be from cardiac-related causes, with sudden death, congestive heart failure, or myocardial infarction accounting for 50% to 60%. (Murphy and Kloster, Oct. 1979-6,20,27). In another paper *Preoperative Exercise Capacity in Symptomatic Patients with Aortic Regurgitation as a Predictor of Postoperative Left Ventircular Function and Long-term Prognosis* (Bonow et al, 1980) the authors were looking at a means of predicting the prognosis of a patient. Using treadmill exercise testing and cardiac studies, the authors were able to take a group of 45 patients and divide them into a low risk and high risk group. In the high risk group of 17 patients, nine died shortly after surgery; 7 of the 9 deaths were from late congestive heart failure. The report concluded that exercise capacity could be used to more actually predict long-term survival after valve replacement. This indicates that it may be possible for clinicians to assess valve replacement candidates and predict which patients are at the greatest risk of congestive heart failure. These individuals with documented increased risk of CHF could be the initial candidates to receive the power assisted valve of the present invention in place of a conventional valve in an attempt to increase their probability of survival.

Turning now to FIG. 5, a schematic diagram is shown of the power assisted prosthetic heart valve in accordance with the present invention. The power assisted heart valve system preferably consists of a pacemaker/cardioverter type device 100, a rechargeable power supply 102 and a transcutaneous means of recharging 104, a set of leads 106 to monitor the cardiac cycle (serving as input to the pacemaker) and a set of leads 108 traveling from the pacemaker 100 to the prosthetic valve 110 which serve to control the electromagnet output from the pacemaker. Following the same path as the output leads 108 from the pacemaker 100, in a preferred embodiment, a third conductor 112 is included to supply a small negative electrical charge to the valve in order to premote a locate anticoagulative effect as will be discussed in greater detail below. Finally, an external recharger 114 located at the surface of the body, may be used in a known manner to recharge battery pack 102. It will be appreciated that the individual components 100, 102, 104 and 114 illustrated in FIG. 5 are all conventional and well known. For example, "through the skin" charging systems are disclosed in U.S Pat. Nos. 3,867,950 and 4,275,739. The monitoring and control circuits of pacemaker device 100 are also known. Controller Device 100 may comprise modified hardware such as implantable cardioverter/defibrillator (described in U.S. Pat. Nos. 4,625,730 or alternatively 4,548,209) or a single or dual chamber multiprogrammable microprocessor based pacemaker (such as Medtronics 7000 series or Vitatron Pacer). The operation of the system illustrated in FIG. 5 has already been set forth in the discussion of FIG. 4.

The power assisted heart valve of the present invention has an additional important feature aimed at the reduction of the thromboembolic phenomena, a major clinical complication of prosthetic heart valves. It has been shown by Saywer (Sawyer et al, 1972, 1975) and others in the 1950's, 60's and early 70's that metals with a negative electrical charge in contact with blood have an anticoagulative effect. The red blood cells and platelets contain negatively charged outer membranes which are repelled by the negatively charged endothelial cells which line the inner surface of blood vessels and in a similar fashion by metal with negatively charged surfaces. In 1972, Sawyer et al published a paper *Antithrombogenic Characteristics of Cathodically Polarized Copper Prostheses* which provided clear evidence that an electrical negative charge could be applied to a metal prosthesis to reduce thrombosis (Sawyer et al, 1975). The favorable effects of a negative charge are also discussed in U.S. Pat. Nos. 3,491,756; 3,609,768; 3,927,422; 4,038,702; 4,082,507 and 4,265,928.

Providing a negative electrical charge to the valve of the present invention in an attempt to reduce thromboembolic phenomena is believed to be a significant feature of the present invention. Thromboembolic complications (strokes) have been a continuing and distressing problem with prosthetic valves (Murphy and Kloster, Nov. 1979 part II). Even the addition of anticoagulants does not eliminate the risk of emboli. In addition, the requirement for chronic Coumadin anticoagulation in most patients invokes a significant risk of bleeding complications. Approximately 70% to 80% of patients on Coumadin will be considered to have adequate control. In the remaining 20% to 30%, control may be erratic and those patients are at increased risk of anticoagulation or thromboembolic complications. The risk of a hemorrage complication in patients on coumadin is 3 to 5.7 per 100 patient-years. The incidence of serious hemorrahagic complications with serious morbidity, or mortality is probably half of that. The use of an electrical charge provides many desirable aspects. For example, a local effect can be produced at the heart valve site and the negative surface charge (for example −160 mV) can be maintained with a high level of accuracy.

The negative electric charge could be used with medication (asprin regimen or coumadin) or possibly could be used to replace medications at times when medications are contradicted. More research is required to determine how extensive a role the use of an electrically supplied charge could contribute to the anticoagulation process in heart valves. Many individuals would benefit a great deal from the ability to decrease medications without significant increased risk of emboli (provided by electrical means). Women who are considering pregnancy could be candidates for electrically charged prosthetic valves. Currently, these women must be taken off coumadin during pregnancy and given daily subcutaneous injections of heparin in its place to maintain anticoagulation. At the time of delivery, the heparin must be stopped for the immediate peripartal period. Despite these precautions, maternal deaths and fetal wastage remain serious problems, primarily because of the anticoagulation and embolic complications. The use of an electrical charge would provide a local effect and would be less likely to interfer with the development and birth of the child. In addition, there are countless other groups of mechanical valve patients who could benefit from the use of an electrically charged valve.

It will be appreciated that the present invention has the potential to require a considerable quantity of energy to function continuously for long durations of time. The presently known preferred solution to this dilemma will involve the use of the recharageable power supply of FIG. 5 as well as placing some restrictions on the use of high energy consuming functions. For example, the power assisted closure could be programmed to operate on a conditional basis (i.e. trigger closure if the heart rate exceeds 100 beats/min). While the heart rate is less than 100 beats/min the valve would close by its normal passive means (pressure gradients).

In addition, negative electric charge could be delivered to the valve surface during pre-selected time intervals in the pump cycle when increased stasis causes thrombosis; or to provide a cushioning effect during moments of maximum turbulence to reduce hemolysis.

It will be further appreciated that the power activated prosthetic valve of the present invention may also be utilized in conjunction with artificial hearts such as the well known JARVIK 7; as well as natural hearts (see Altieri et al, Mechanical Support for the Failing Heart, Journal of Biomaterials Applications, Vol. 1, 106–156, July 1986).

The power assisted valve could be utilized in Implantable Total Artificial Hearts such as the Pennsylvania State University (PSU) and the University of Utah (UU) devices to improve their pumping function. Both devices use separate right and left ventricles and must meet the fundamental requirement of delivering balanced ventricular outputs. The problem of delivering balanced ventricular outputs is complicated by two factors. The first is the presence of an anatomic left-to-left shunt due to bronchial artery flow. Thus, equal cardiac outputs from the ventricles would actually yield the right heart outpumping the left heart. The second factor is that prosthetic valve regurgitation losses and housing compliance losses are greater for the left ventricle than for the right.

The PSU device balances the outputs for left and right pumps using a stroke-time division process. The stroke volume of the right pump can be controlled at less than 100% to prevent over pumping imbalances. The UU device utilizes a control system feedback loop in conjunction with a right-to-right shunt of a modified Bjork-Shiley pulmonic valve to compensate for the left-to-left shunt of the bronchial artery flow and the greater left side losses. By decreasing the disk diameter, the annular area between the disk and valve ring is increased, and closed valve backflow (regurgitation) is thus larger than for a normal valve and the right sided pumping action is reduced to match the left side.

The power assisted valve could be utilized to reduce and/or control the degree of regurgitation in the left ventricle to achieve ventricle output balance. In addition, the reduction in regurgitation will increase the efficiency of the pump and allow for longer intervals between charging the battery supply.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A power assisted heart valve comprising:
   heart valve means, said heart valve means including an annular frame means for attachment to a vessel wall and closure means mounted to said frame means wherein said closure means freely opens and closes the annulus in said annular frame means; and
   electromagnetic means associated with said closure means; and
   triggering means electrically connected to said electromagnetic means for selectively electrically powering said electromagnetic means at a pre-selected moment in the pump cycle to thereby initiate accelerated closure of said heart valve means.

2. The heart valve of claim 1 wherein said electromagnetic means comprises:
   permanent magnet means movable with said closure means; and
   electromagnet means attached to said frame means.

3. The heart valve of claim 1 wherein:
   said pump cycle comprises a cardiac cycle.

4. The heart valve of claim 3 wherein said triggering means comprises:
   monitoring means for monitoring the cardiac cycle;
   battery means for storing electrical power; and
   control means for delivering electrical power from said battery means to said electromagnetic means in response to a signal from said monitoring means.

5. The heart valve of claim 4 wherein said battery means is rechargeable and including:
   first recharging circuit means connected to said battery means and including a first coil; and
   second recharging circuit means having a second coil for remote communication with said first coil of said first recharging circuit means.

6. The heart valve of claim 3 including:
   means for synchronizing said triggering means with the electrocardiogram (EKG) of the cardiac cycle.

7. The heart valve of claim 1 including:
   means for providing a negative electrical charge to said heart valve means.

8. The heart valve of claim 2 wherein:
   said closure means comprises a disc pivotably mounted in said frame means; and
   said permanent magnet means is mounted on said disc.

9. The heart valve of claim 2 wherein:
   said closure means comprises a pair of opposed semicircular plates pivotably mounted in said frame means; and
   said permanent magnet means comprises at least one magnet, mounted on each of said semi-circular plates.

10. The heart valve of claim 2 wherein:
    said electromagnet means is mounted on a rigid arm extending from said frame means.

11. The heart valve of claim 1 including:
    means for decelerating the accelerated closure of said heart valve means at a pre-selected moment in the pump cycle.

12. A power assisted heart valve comprising:
    heart valve means, said heart valve means including an annular frame means for attachment to a vessel wall and closure means mounted to said frame means wherein said closure means freely opens and closes the annulus in said annular frame means;
    electromagnetic means associated with said closure means; and
    triggering means electrically connected to said electromagnetic means for selectively activating said electromagnetic means at a pre-selected moment in the cardiac cycle to thereby initiate accelerated closure of said heart valve means, said triggering means comprising;
    monitoring means for monitoring the cardiac cycle;
    battery means for storing electrical power; and
    control means for delivering electrical power from said battery means to said electromagnetic means in response to a signal from said monitoring means.

13. The heart valve of claim 12 wherein said battery means is rechargeable and including:
    a first recharging circuit means connected to said battery means and including a first coil; and
    second recharging circuit means having a second coil for remote communication with said first coil of said first recharging circuit means.

14. A power assisted heart valve comprising:
    heart valve means, said heart valve means including an annular frame means for attachment to a vessel wall and closure means mounted to said frame means wherein said closure means freely opens and closes the annulus in said annular frame means;
    electromagnetic means associated with said closure means, said electromagnetic means comprising permanent magnet means movable with said closure means and electromagnet means attached to said frame means;
    triggering means electrically connected to said electromagnetic means for selectively activating said electromagnetic means at a pre-selected moment in the pump cycle to thereby initiate accelerated closure of said heart valve means; and
    said electromagnet means being mounted on a rigid arm extending from said frame means.

15. A heart valve comprising:
    heart valve means, said heart valve means including an annular frame means for attachment to a vessel wall and closure means amounted to said frame means wherein said closure means freely opens and closes the annulus in said annular frame means; and
    means for providing a negative electrical charge to said heart valve means at preselected intervals of a cardiac pumping cycle.

* * * * *